US010881482B2

(12) United States Patent
Rauniyar et al.

(10) Patent No.: US 10,881,482 B2
(45) Date of Patent: Jan. 5, 2021

(54) OPERATING ROOM DEVICES, METHODS, AND SYSTEMS

(71) Applicant: Boston Scientific Scimed, Inc., Maple Grove, MN (US)

(72) Inventors: Niraj Rauniyar, Plymouth, MN (US); Timothy Harrah, Cambridge, MA (US); Peter J. Pereira, Mendon, MA (US); Eric Wong, South Grafton, MA (US); William Stanhope, Lunenburg, MA (US); Brian MacLean, Cary, NC (US); Brandon Craft, Edgewater, MD (US); Stuart Perry, Wellesley Hills, MA (US); William Gastrock, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 262 days.

(21) Appl. No.: 15/974,403

(22) Filed: May 8, 2018

(65) Prior Publication Data
US 2018/0325619 A1 Nov. 15, 2018

Related U.S. Application Data

(60) Provisional application No. 62/503,774, filed on May 9, 2017.

(51) Int. Cl.
*A61B 90/00* (2016.01)
*G16H 40/63* (2018.01)
*G16H 20/40* (2018.01)
*A61B 17/00* (2006.01)
*A61B 1/04* (2006.01)

(52) U.S. Cl.
CPC ............ *A61B 90/37* (2016.02); *A61B 90/361* (2016.02); *G16H 20/40* (2018.01); *G16H 40/63* (2018.01); *A61B 1/04* (2013.01); *A61B 2017/00199* (2013.01); *A61B 2017/00221* (2013.01)

(58) Field of Classification Search
USPC .......................................................... 606/2
See application file for complete search history.

(56) References Cited

U.S. PATENT DOCUMENTS

2007/0066911 A1  3/2007  Klingenbeck-Regn
2010/0286520 A1* 11/2010  Hazard ................... A61B 8/06
                                                              600/439

FOREIGN PATENT DOCUMENTS

WO    WO 2014/062219 A1    4/2014

OTHER PUBLICATIONS

International Search Report and Written Opinion for corresponding International Application No. PCT/US2018/031655, dated Jul. 11, 2018 (12 pages).

* cited by examiner

*Primary Examiner* — Nadia A Mahmood
(74) *Attorney, Agent, or Firm* — Bookoff McAndrews, PLLC

(57) ABSTRACT

Operation room devices, methods, and systems are disclosed. One method comprises: receiving, at a processing unit, data associated with a patient; determining, with the processing unit, a treatment for the patient; identifying, with the processing unit, a control setting associated with one or more treatment devices that are (i) in communication with the processing unit, and (ii) operable to perform the treatment; and generating, with the processing unit, a display including the control setting and at least one view of the data. Related devices and systems also are disclosed.

19 Claims, 11 Drawing Sheets

OPERATING ROOM DEVICES, METHODS, AND SYSTEMS

CROSS-REFERENCE TO RELATED APPLICATIONS

This patent application claims the benefit of priority under 35 U.S.C. § 119 to U.S. Provisional Patent Application No. 62/503,774, filed May 9, 2017, which is herein incorporated by reference in its entirety.

TECHNICAL FIELD

Aspects of the present disclosure generally relate to operating room devices, methods, and systems. Some aspects are suitable for urological procedures.

BACKGROUND

Numerous treatment devices may be used in a typical urological procedure to diagnose conditions and perform treatments (e.g., kidney stone management, BPH treatments, prostatectomies, tumor resection, uterine fibroids management, etc.). Each treatment device (e.g., a fluid source or a laser source) may rely upon specific input (e.g., flow rate or power level). These inputs are typically provided with device specific controls, such as a keypad attached to a source module (e.g., the fluid source or laser source) located outside of the operating room.

To perform certain treatments, a surgeon may be required to configure and operate each of these treatment devices, individually and/or in combination. For example, a single urological procedure may employ multiple scopes, each having their own display and controls; multiple treatment devices, each having their own display and controls; and multiple patient monitoring devices, each having their own display and controls—all of which must be coordinated during the various stages of a typical procedure. Procedural inefficiency can be attributable to non-communication between these devices at each stage, increasing operating times and costs. For example, the surgeon may be required to either operate each device separately, requiring mastery of many devices; and/or utilize an assistant to operate one or more of the devices, increasing the communication burden. Administrative efficiency after the procedure can also be reduced, for example, by requiring staff to separately record the use of each device, further increasing effort and costs.

Aspects of the operating room devices, methods, and systems described herein may address these issues, and/or other deficiencies of the art.

SUMMARY

One disclosed aspect is a method. For example, the method may comprise: receiving, at a processing unit, data associated with a patient; determining, with the processing unit, a treatment for the patient; identifying, with the processing unit, control settings associated with one or more treatment devices that are (i) in communication with the processing unit, and (ii) operable to perform the treatment; and generating, with the processing unit, a display including the control settings and at least one view of the data. Numerous aspects of exemplary methods are now described.

According to some aspects, the data may include a three-dimensional model of a portion of the patient, and the receiving step may comprise: receiving, at the processing unit, the three-dimensional model from a data source; and selecting, with the processing unit, the at least one view from the three-dimensional model. The data may include images of the patient, and the receiving step may comprise: receiving, at the processing unit, the images from the data source; and/or generating, with the processing unit, a three-dimensional model of the patient from the images. The determining step may further comprise: identifying, with the processing unit, potential treatments for the patient; determining, with the processing unit, whether the one or more treatment devices are operable to perform the potential treatments; and generating, with the processing unit, the display to include a listing of the potential treatments performable by one or more treatment devices.

In some aspects, the identifying step may comprise obtaining, with the processing unit, the control settings from the one or more treatment devices. For example, the identifying step may comprise: receiving, at the processing unit, a device identifier from the one or more treatment devices; delivering, with the processing unit, the device identifier to a data source; and receiving, at the processing unit, the control settings from the data source. The one or more treatment devices may include a first treatment device in communication with the processing unit and a second treatment device in communication with the processing unit. Accordingly, the identifying step may further comprise: receiving, at the processing unit, a first control setting for the first treatment device and a second control setting for the second treatment device; and identifying, with the processing unit, one or more computer applications for operating the first and second treatment devices in a coordinated manner to perform a treatment. For example, identifying the one or more computer applications may comprise: delivering, with the processing unit, the first and second control settings to a data source; and receiving, from the data source, the one or more applications configured to operate the first and second devices simultaneously.

The at least one view may include a first view different from a second view, and the generating step may comprise: positioning a distal end of the one or more treatment devices in the patient; and locating, with the processing unit, said distal end in the first and second views. For example, the distal end of the treatment may include a locator beacon, and the processing unit may include a tracking module configured to identify the locator beacon in the first and second views. The data may include images of interior surfaces of the patient, the first view may include the interior surfaces, and the method may comprise: overlaying, with the processing unit, a grid onto the interior surfaces depicted in the first view of the patient; tagging, with the processing unit, at least one area defined by the grid; and locating, with the processing unit, the at least one area in the second view of the patient.

According to some aspects, the method may comprise: receiving, with the processing unit, an input from an input device in communication with processing unit; and operating, with the processing unit, the treatment device according to the input and the control setting, wherein the input is a user-generated signal including at least one of an audio signal, a tactile signal, and a visual signal. The method may further comprise: identifying, with the processing unit, an object in the patient; and locating, with the processing unit, the object in the at least one view. The generation step may comprise: determining, with the processing unit, a characteristic of the object using at least one sensor; and modifying, with the processing unit, the input or the control settings based on the characteristic. In addition, the method may further comprise: generating, with the processing unit, one or more reports including the control settings and the input; and outputting, with the processing unit, the one or more reports.

Another disclosed aspect is a method. For example, this method may comprise: generating, with a processing unit, a display including control settings for a treatment device and at least one view of data associated with a patient; overlaying onto the at least one view, with the processing unit, depictions of (i) a treatment site, (ii) a path to the treatment site, and (iii) a location of the treatment device on the path; moving the treatment device along the path responsive to the display, and continuously updating the display with processing unit responsive to the movements, until the location of treatment device arrives at the treatment site; obtaining from an input device, with the processing unit, an input responsive to the control settings; and operating, with the processing unit, the treatment device to apply a treatment energy at the treatment site according to the input and the control settings. Numerous aspects of exemplary methods are now described.

According to some aspects, the input may comprise a user-generated signal including at least one of an audio signal, a tactile signal, and a visual signal; and the method may further comprise: converting, with the processing unit, the user-generated signal into a control signal; and outputting, with the processing unit, the control signal to the treatment device. The method may further comprise: determining, with the processing unit, a characteristic of the object or the treatment energy using one or more sensors; and modifying, with the processing unit, the control signal based on the determined characteristic. For example, the method may comprise: obtaining, with the processing unit, a computer application configured for use with the one or more sensors; and determining, with the processing unit, the characteristic with the computer application and one or more sensors. The object may include one or more stones, the characteristic may include a measure of stone burden, stone size, or stone type associated with the one or more stones, and the computer application may be configured to modify the control signal based on the measure. The characteristic also may include the composition of the one or more stones, and the computer application may be configured to modify the control signal based on the composition. In some aspects, the treatment energy may comprise a laser energy, the characteristic may include a measure of the laser energy, and the computer application may be configured to modify the control signal based on the measure of the laser energy.

Another disclosed aspect is a system. For example, the system may comprise: a processing unit in communication with one or more treatment devices; a display generated by the processing unit to comprise at least one view of data associated with a patient, and control settings for the one or more treatment devices; and an input device operable with the display to receive an input responsive to the control settings, and activate the one or more treatment devices. Numerous aspects of exemplary systems are now described.

According to some aspects, the processing unit may be configured to: obtain the data from a data source; and obtain the control settings from the treatment device or the data source. The data may include a three-dimensional model of a portion of the patient, and the processing unit may be configured to generate the at least one view based on three-dimensional model. For example, the data may include images of the patient, and the processing unit may be configured to: obtain, from a data source, a computer application configured to generate the three-dimensional model from the images; and/or generate the three-dimensional model with the application.

The processing unit may be configured to: identify capabilities associated with the one or more treatment devices; obtain, from a data source, a computer application based on the identified capabilities; and generate the control settings with the computer application. The one or more treatment devices may include a first treatment device and a second treatment device, and the control settings may include at least one option for operating the first and second treatment devices in a coordinated manner to perform a treatment. For example, the first treatment device may be a laser source, the second treatment device may be a fluid source, and the at least one option may be configured to operate the laser source and fluid source according to a predetermined sequence.

Another disclosed aspect is an input device. For example, a treatment device may include a handle, and the input device may include a display actuator mounted on the handle and operable with the at least one view. The treatment device may be a scope, and the handle may include the display actuator and one or more scope actuators configured to operate a steerable portion of the scope. The input device may be configured to receive a user-generated signal including at least one of audio signal, a tactile signal, and a visual signal. For example, the input device may include one or more sensors configured to receive the user-generated signal, such as a display actuator with one or more buttons configured to receive the tactile signal, or a movement sensor configured to receive the visual signal by tracking movements of the display actuator or the user. In one aspect, one of the above-described systems further comprises a projector configured to output the display onto a surface, and the input device may comprise an eye movement sensor configured to receive the visual signal by tracking movements of at least one eye of a user relative to the surface. For example, the surface and/or the eye movement sensor may be head-mounted so as to position the display and sensor within a field of view of the least one eye.

It is understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more exemplary aspects according to this disclosure, as follows.

DETAILED DESCRIPTION

Figure 1:
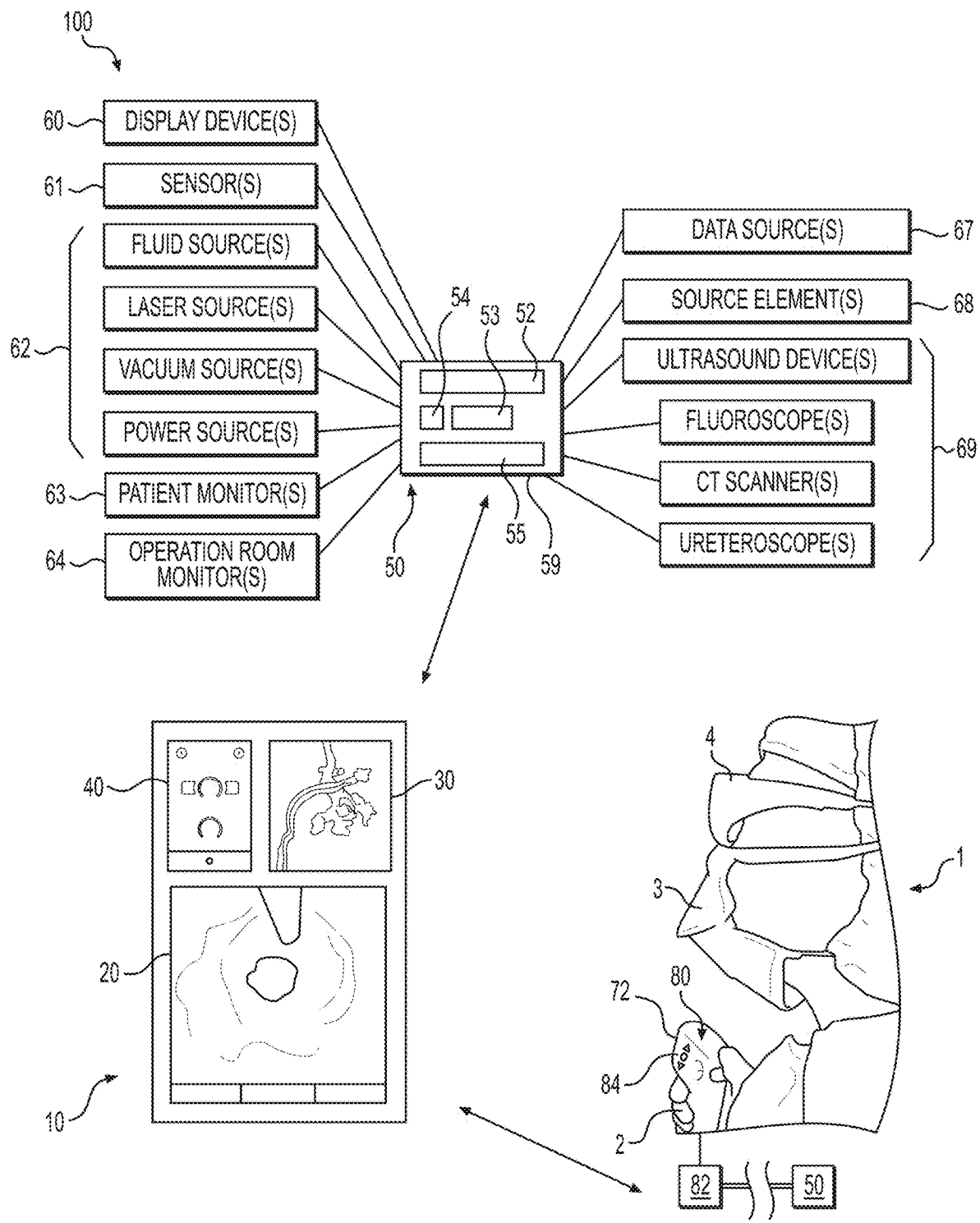
FIG. 1 depicts aspects of an exemplary system.

Aspects of the present disclosure are now described with reference to operating room devices, methods, and systems.

Some aspects are described with reference to urological procedures, wherein a treatment device (e.g., a scope) may be advanced through a path or passage in a body (e.g., a ureter) for removal of an unwanted object (e.g., a stone) from a cavity in the body (e.g., a calyx of a kidney). References to a particular type of procedure, such as a urological procedure; treatment device, such as a scope; unwanted material, such as a stone; or bodily part, such as a ureter, are provided for convenience and not intended to limit this disclosure. Accordingly, the devices, methods, and systems described herein may be utilized for any analogous purposes—medical or otherwise.

The terms "proximal" and "distal," and their respective initials "P" and "D," may be utilized along with terms such as "parallel" and "transverse" to describe relative aspects in this disclosure. Proximal refers to a position closer to the exterior of the body (or closer to a user), whereas distal refers to a position closer to the interior of the body (or further away from the user). Appending the initials "P" or "D" to an element number signifies a proximal or distal location or direction. The term "elongated" as used herein refers to any object that is substantially longer in relation to its width, such as an object having a length that is at least two times longer than its width. Unless claimed, however, these terms are provided for convenience and not intended to limit this disclosure to a particular location, direction, or orientation.

As used herein, terms such as "comprises," "comprising," or like variations, are intended to cover a non-exclusive inclusion, such that any aspect that comprises a list of elements does not include only those elements or steps, but may include other elements or steps not expressly listed or inherent thereto. Unless stated otherwise, the term "exemplary" is used in the sense of "example" rather than "ideal." Conversely, the terms "consists of" and "consisting of" are intended to cover an exclusive inclusion, such that an aspect that consists of a list of elements includes only those elements. As used herein, terms such as "about," "substantially," "approximately," or like variations, may indicate a range of values within +/−5% of a stated value.

Aspects of hardware and software are disclosed. Accordingly, some aspects may be entirely hardware, entirely software, or a combination of hardware and software. Some aspects may be described as a computer application, such as a computer program product stored on a computer-usable data storage medium or data source. Such applications may be executed by one or more processors in communication with the data source. Any data source may be utilized, including hard disks, CD-ROMs, optical storage devices, or other electronic, magnetic, optical, electromagnetic, infrared, or semiconductor system, apparatus, device, or like propagation medium.

Any combination of local or remote resources for data processing and storage may be used to execute the described applications, including the combinations described herein. The relative locations of these resources may be optimized to realize useful advances in processing power. For example, the one or more processors may be local to an operating room, such as behind a sterile field; and the data source may be remote from the operating room, such as at a server farm located miles away. Accordingly, some described aspects are particularly useful when obtaining large amounts data from the data source in real-time, such as during a urological procedure. Unless claimed, however, these terms are provided for convenience and not intended to limit this disclosure to a particular location and/or relativity.

Figure 2A:
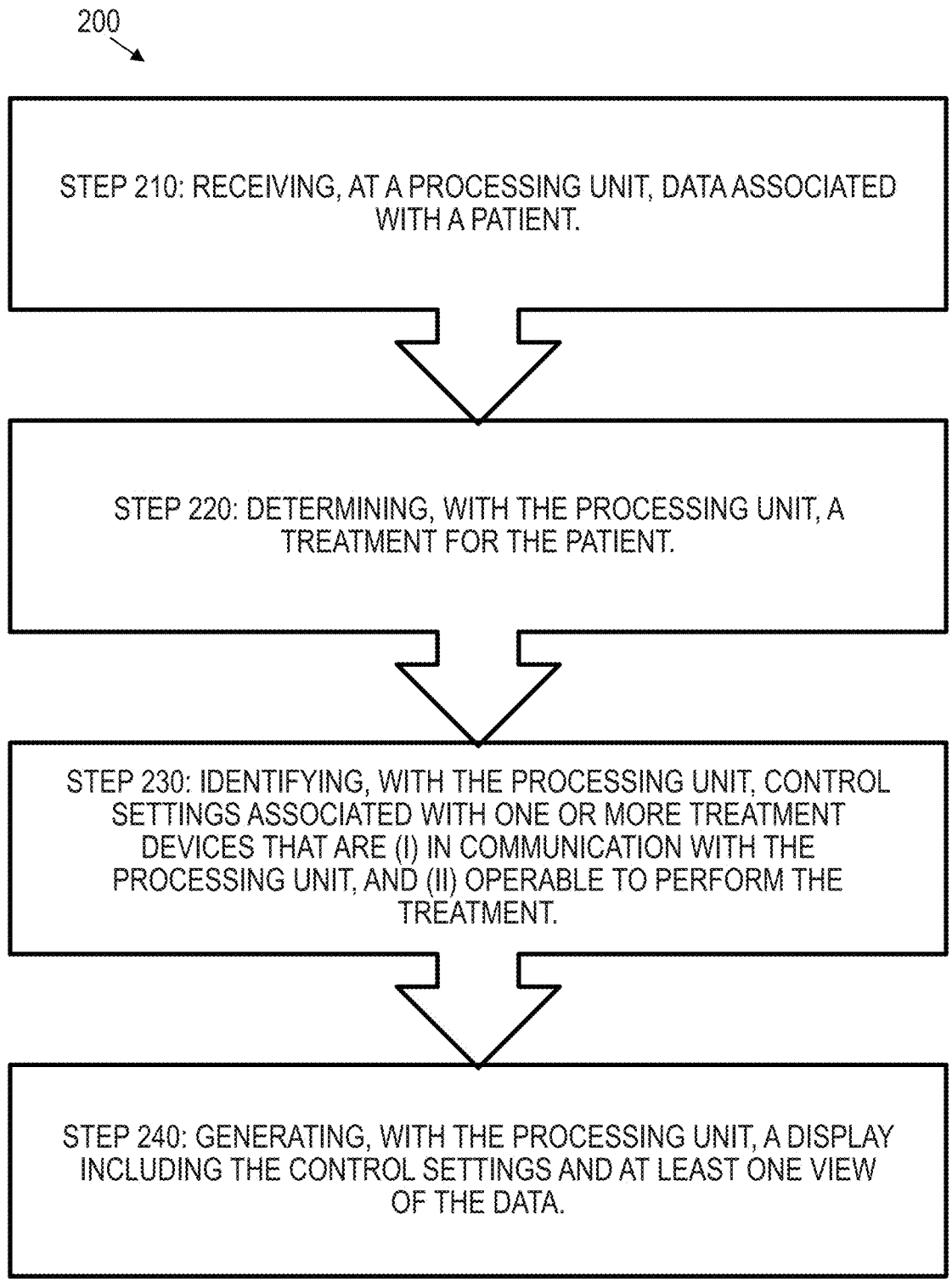
FIGS. 2A-C depict aspects of exemplary methods.
Figure 2B:
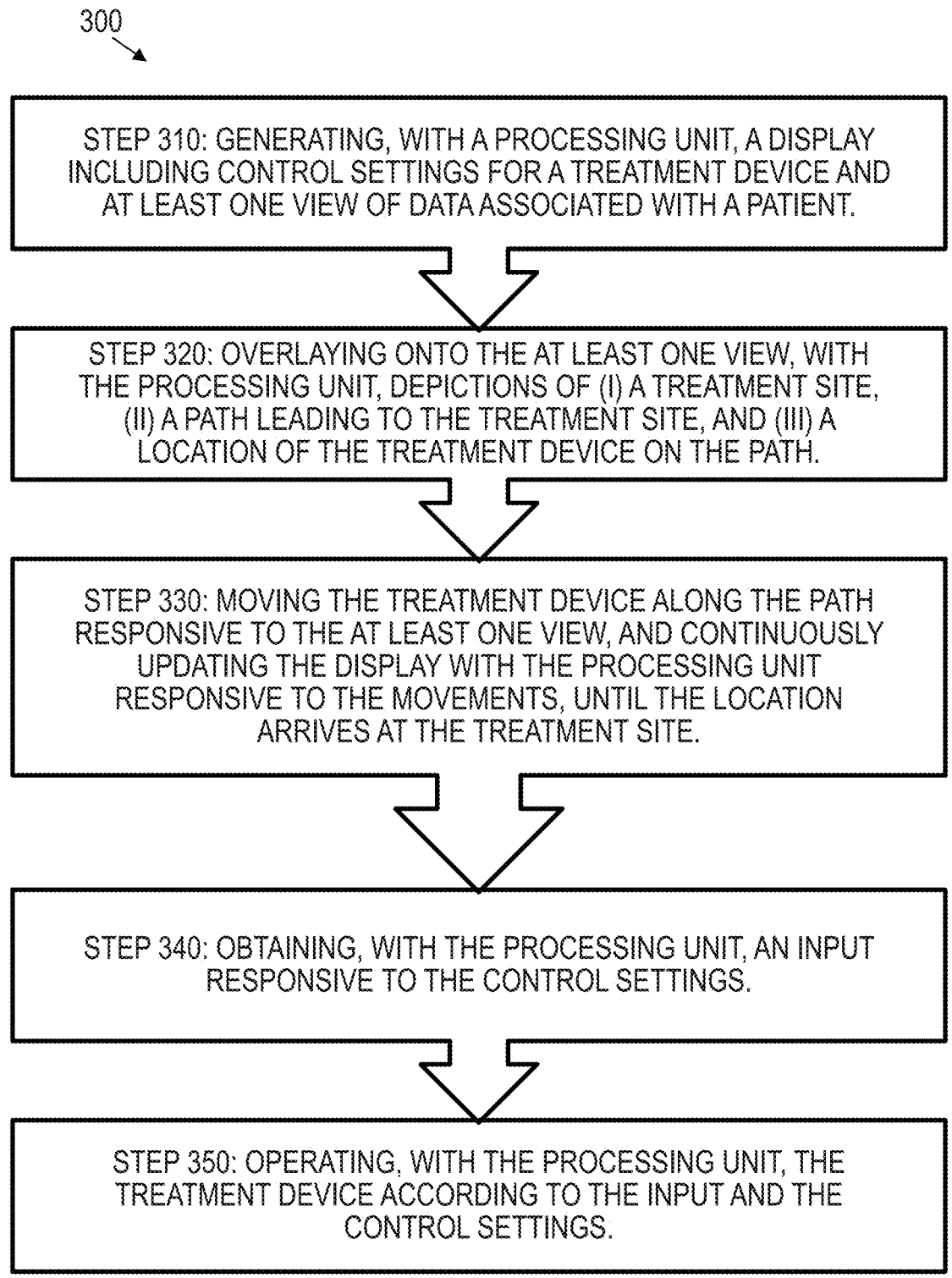
Figure 2C:
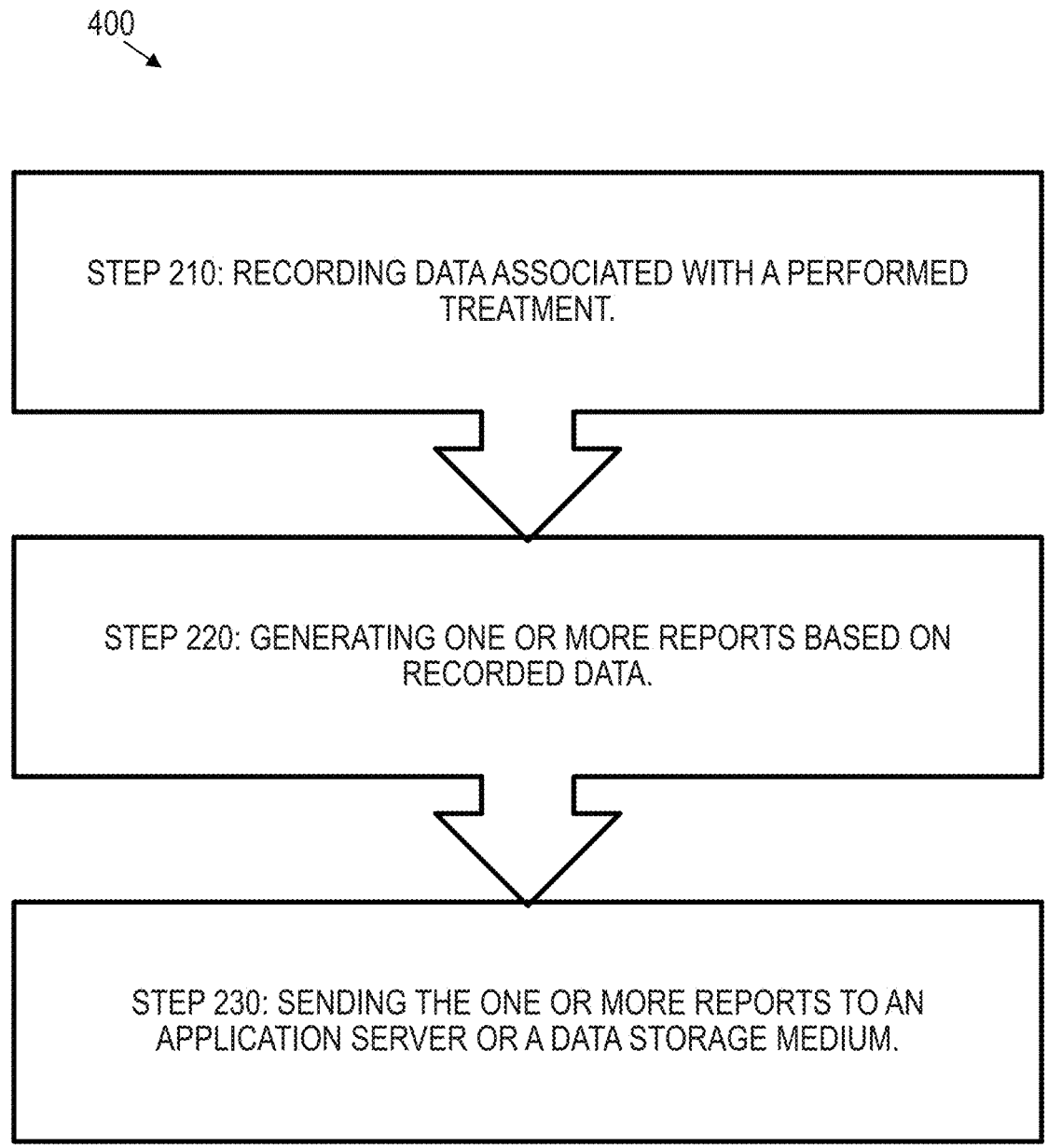

Some aspects may be described using conceptual and/or flowchart illustrations, such as the exemplary method steps depicted in FIGS. 2A-C. Although such illustrations may include sequential depictions, many steps can be performed in parallel, performed concurrently, or omitted entirely, including those in FIGS. 2A-C. The order of the steps also may be re-arranged. A method may be terminated when the last step is performed, but also could have additional steps, including the intermediate steps described herein and/or any configuration steps inherent to the performance of a procedure or use of a technology. Some of the described methods and/or method steps may be realized as computer applications, executable by one or more processors (e.g., a microprocessor, microcontroller, or the like); while other methods and/or method steps may be realized as surgical methods, performable by a human operator or user (e.g., a surgeon). Other methods and/or steps may be realized as a combination thereof.

Numerous aspects of the present disclosure are now described with reference to a base system 100. An exemplary base system 100 is depicted in FIG. 1. Base system 100 may be used to perform numerous operating room methods, including exemplary methods 200, 300, and 400 described below. As shown, aspects of base system 100 may comprise: a display 10; a processing unit 50 configured to generate display 10 using one or more computer applications; and an input device 80 configured to operate display 10. A user 1 (e.g., a surgeon) is also depicted in FIG. 1 as having a hand 2, a mask 3, and a pair of glasses 4. Numerous aspects of base system 100 are now described, followed by: a detailed description of methods 200, 300, and 400; additional aspects system 100; and additional aspects of input device 80.

Display 10 may comprise at least one view of data associated with a patient, and at least one view of one or more control settings associated with one or more treatment devices. In FIG. 1, for example, display 10 comprises a first or navigation view 20 of the patient; a second or map view 30 of the patient; and a third or control view 40 of control settings for a treatment device. The at least one view may be based on any data associated with the patient. Exemplary data types may comprise: (i) image data, such as still frame or video files of the patient generated by the one or more imaging devices 69; (ii) sensory data, such as characteristics of an object inside the patient determined by one or more sensors 61; and (iii) geometric data, such as a three-dimensional model based on any image and/or sensor data associated with at least portion of the patient. Any type of data may be received by processing unit 50 in real-time (e.g., accessed from a live video feed) and/or in advance (e.g., downloaded from a remote server) from any data source local to or remote from system 100.

Figure 4A:
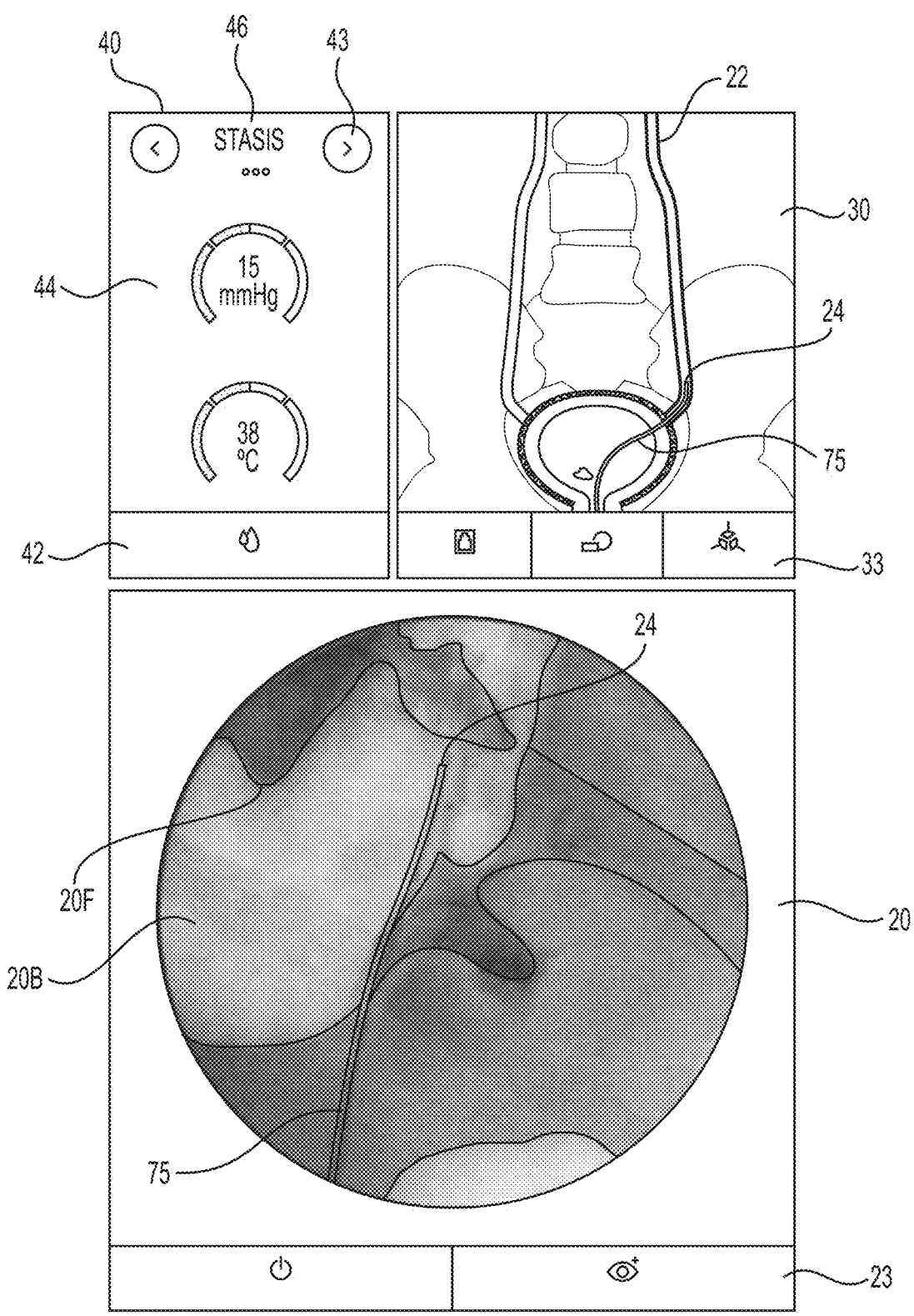
FIGS. 4A-C depict additional aspects of an exemplary display.
Figure 4B:
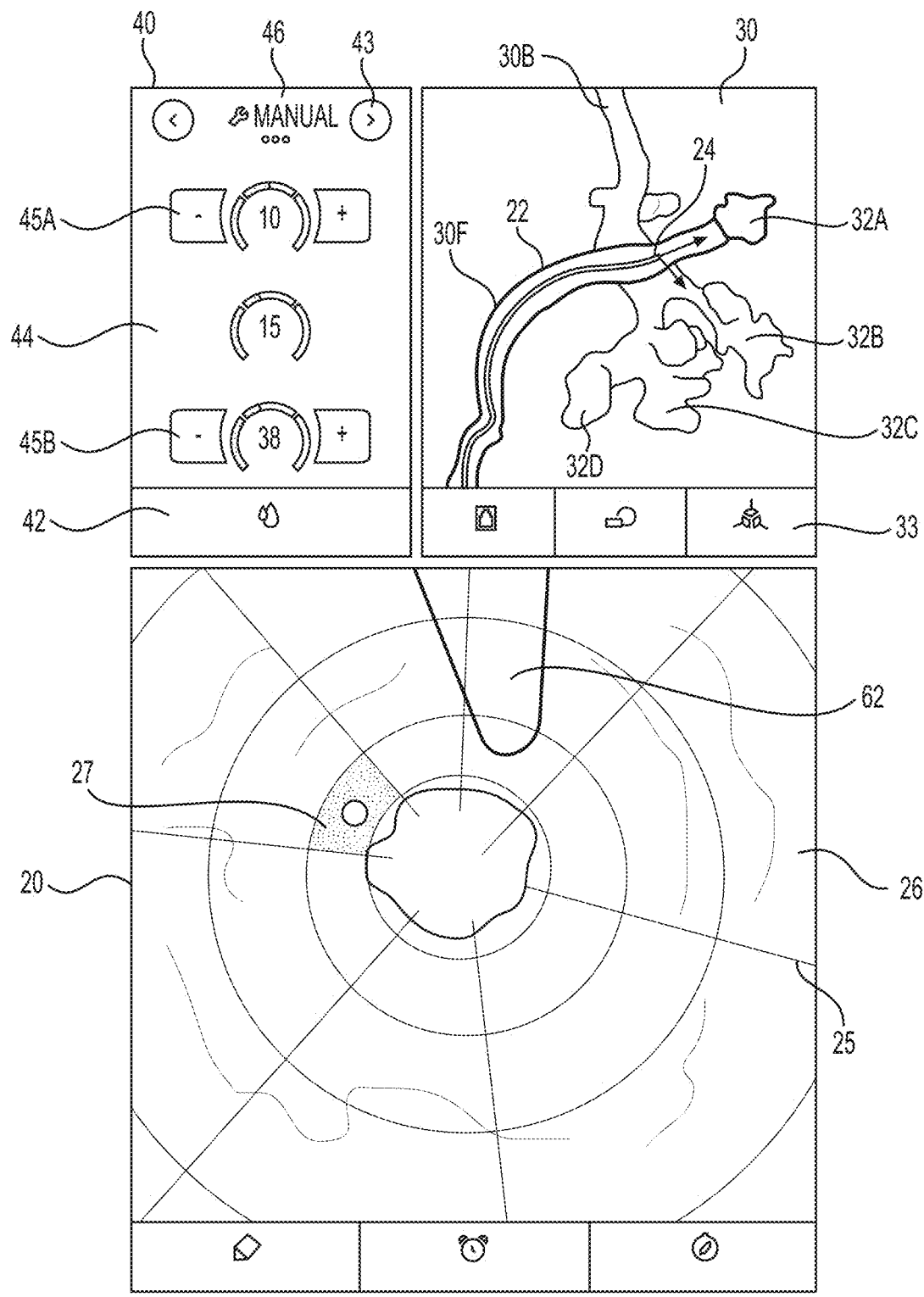
Figure 4C:
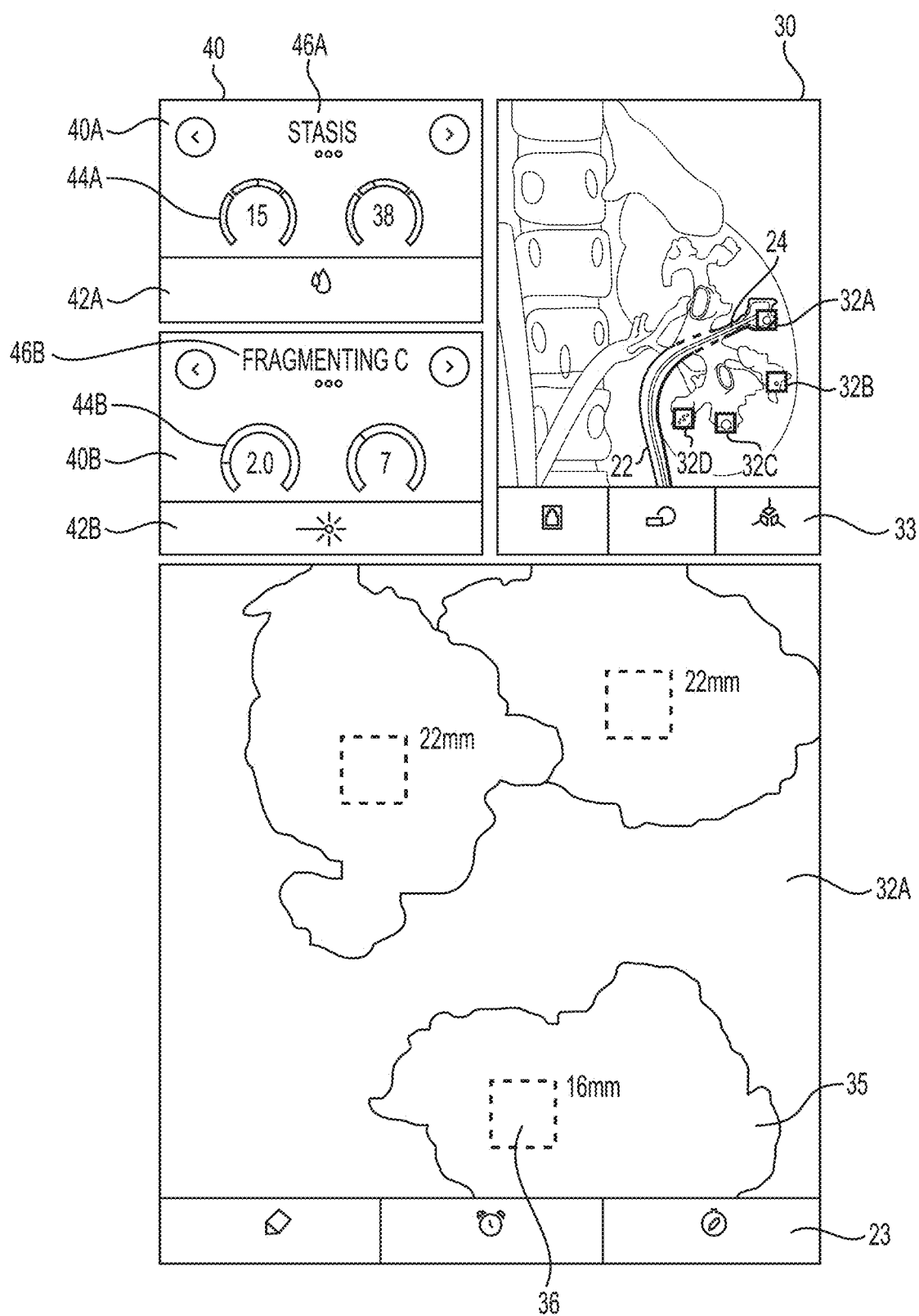

Navigation view 20 and map view 30 may be generated from the same or different types of data. As shown in FIG. 4A, for example, navigation view 20 may be generated from fluoroscopic images of a patient, while map view 30 may be generated from a first view of a three-dimensional model of the patient. Additional examples of display 10 are depicted in FIG. 4B, wherein navigation view 20 may be generated from a real-time video feed of a path extending through the patient, and map view 30 may be generated from a second view of the three-dimensional model of the patient; and FIG. 4C, wherein navigation view is 20 may generated by an output from one or more sensors 61 located in the path, and map view 30 is generated from a third view of the three-dimensional model of the patient. The data types may be grouped and/or layered to create the at least one view. Display 10 may be further configured for switching between different views, types, groupings, and/or layers. For example, as shown in FIGS. 4A-C, each navigation view 20 and map view 30 may be switchable between different data types using their respective toggle switches 23 and 33.

Control view 40 may be generated by processing unit 50 using data associated with any device. As shown in FIG. 4A, control view 40 may be configured with using with a treatment device 62 by including an activation switch 42, a performance indicator 44, and a status indicator 46. With control view 40 of FIG. 4A, for example: the one or more treatment devices 62 may include a fluid source (e.g., a fluid pump or a pressure bag fitted over a saline bag); switch 42 may activate the fluid source; indicator 44 may continuously monitor fluid pressure and temperature using one or more sensors 61; and status indicator 46 may confirm an operating mode for the fluid source (e.g., stasis). Control view 40 may be similarly configured to control any device depicted in FIG. 1 and/or described herein. For example, view 40 may be configured to control any treatment device 62, any device 62 together with another device, and/or any source element 68 for the device 62, such as a source of fluid, medicine, vacuum pressure, etc. Any device described herein may be considered a treatment device in some urological procedures.

Each treatment device 62 may have its own control settings, and control view 40 may include a toggle switch 43 for switching between one or more settings of the control settings. For example, in FIG. 4B, one treatment device 62 may be a laser source, and control view 40 may be switched to generate a laser energy with the laser source, such that switch 42 now generates the laser energy, indicator 44 now monitors power levels of the laser source, and status indicator 46 now confirms an operating mode for the laser source (e.g., manual). A dual-use example of control view 40 is depicted FIG. 4C, wherein control view 40 comprises: a first control setting 40A with a first activation switch 42A, a first performance indicator 44A, and a first status indicator 46A for the fluid source; and a second control setting 40B with a second activation switch 42B, a second performance indicator 44B, and a second status indicator 46B for the laser source. According to these aspects, any number of devices may be controlled with other multi-use configurations of view 40.

Processing unit 50 may communicate with a plurality of devices, receive data from one or more of the devices, generate display 10 from the data, and control one or more of the devices with display 10 and/or input device 80. As shown in FIG. 1, a non-exclusive listing of the plurality of devices may include: one or more display devices 60 (e.g., a touchscreen display); one or more sensors 61 (e.g., an ultrasound transducer, a pressure sensor, or a temperature sensor); one or more treatment devices 62 (e.g., a fluid source or a laser source); one or more patient monitors 63 (e.g., a vital signs monitor); one or more operating room monitors 64 (e.g., an operating room camera); one or more data sources 67 (e.g., a remote server for storing and access electronic medical records or pre-operative images); one or our more source elements 68 (e.g., a medicine source); and/or one or more imaging devices 69 (e.g., a fluoroscope). Any equivalent device(s) may likewise be included on the list and/or depicted on FIG. 1.

Figure 5:
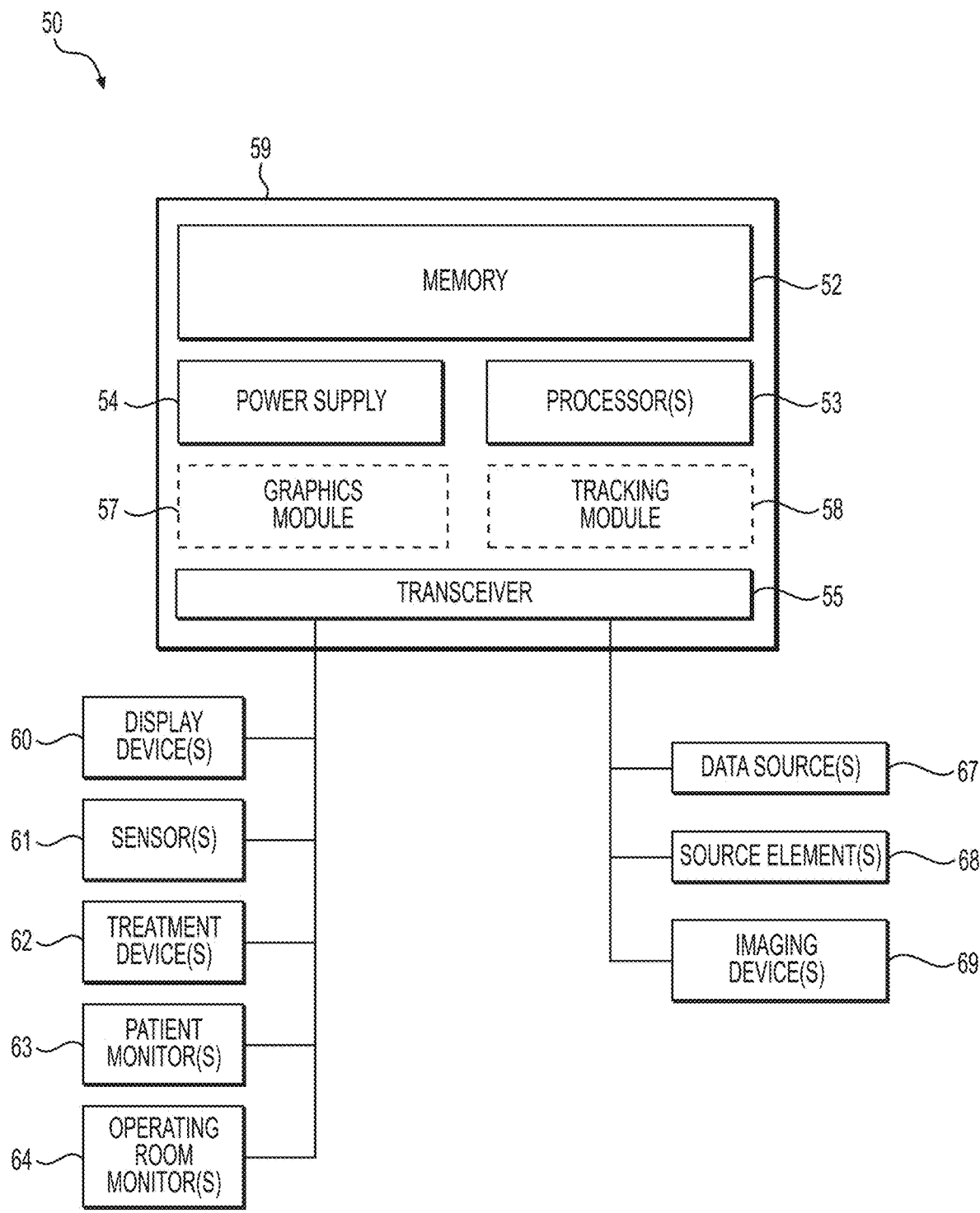
FIG. 5 depicts aspects of an exemplary processing unit.

An exemplary circuit architecture for processing unit 50 is depicted in FIG. 1. Additional aspects of this architecture are depicted in FIG. 5, which includes a number of optional elements described below in relation to methods 200, 300, and/or 400. As shown in FIG. 1, processing unit 50 may comprise: a memory 52; one or more processors 53 configured to execute computer applications; and a transceiver 55 configured to communicate with the plurality of devices. Portions of memory 52 and/or processors 53 may be remote from processing unit 50, yet in constant communication therewith via transceiver 55. For example, one portion of the computer applications may be stored locally on memory 52 and executed locally by processors 53, such as code for display a view of a three-dimensional on a display device 60; while another portion(s) of said computer programs may be stored and executed remotely by a data source 67, such as code for generating the three-dimensional model from image and/or sensor data using a remote application server. Transceiver 55 may be configured to established and maintain communications between processing unit 50 and any device using any known technologies, wired and/or wireless.

Processing unit 50 may serve as a local communication and control hub for base system 100, configured for use in the operating room, behind the sterile field. Unit 50 may be a stand-alone device. For example, as shown in FIG. 1, each of the memory 52, one or more processors 53, and transceiver 55 may be powered by a power source 54 and sealed within an exterior housing 59. Power source 54 may include a battery, a power cord, and/or a local power generation resource. Housing 59 may include a sealed exterior shell and/or one or more sealable ports, allowing processing unit 50 to be sterilized (e.g., wiped down) prior to use within the sterile field. Alternatively, housing 59 may be sealable within a sterile shell (e.g., a disposable case or cover) without hindering the performance of transceiver 55. Housing 59 also may include an attachment portion, such as a clamp engageable with a support structure (e.g., an operating bed); or a clip engageable with user 1, making unit 50 wearable.

Processing unit 50 also may be part of another device. For example, processing unit 50 may be formed integral with: a sensor 61, allowing for more direct receipt of sensor data; or an imaging device 69, allowing for more direct receipt of image data (e.g., a real-time feed of fluoroscopic images). For a urology procedure, for example, unit 50 may be formed integral with a vitals monitoring device, allowing for direct receipt of sensor data associated with the patient's vitals (e.g., an EKG signal); or integral with a fluoroscope, allowing for direct receipt of image data including fluoroscopic images of the patient. Processing unit 50 may also be a peripheral attachment for another device. For example, memory 52 and processors 53 may be housed in a USB stick, and transceiver 55 may be configured to establish communications with the one more devices using WiFi and/or USB protocols. Processing unit 50 may be similarly incorporated into any device described herein.

Many functions of processing unit 50 described herein may be performed with one or more computer applications. Some portion of these applications may be stored on memory 52. Data sources 67 may be used to enhance the capabilities of processing unit 50 and/or memory 52 by providing and/or executing all or portions of the computer applications. In some aspects, data sources 67 may serve as an application store configured to promote selection of a computer applications via processing unit 50, and support the ongoing development of such applications. The various capabilities of each device in communication with processing unit 50 may guide the selection. For example, data sources 67 may be used to: provide and/or update computer applications that are stored locally on memory 52 and configured to identify the capabilities of any device in communication with processing unit 50; provide specialized applications configured to leverage the combined capabilities of one or more devices in communication with unit 50, including any combination of sensors 61, treatment devices 62, and/or imaging devices 69; execute analytical applications that would otherwise exceed the local capabilities of processors 53, including the diagnostic and feedback control methods described herein; and access any capabilities provided by third party computer applications, such as applications for environmental control of the operating room, inventory tracking and management, operating room monitoring.

Figure 6A:
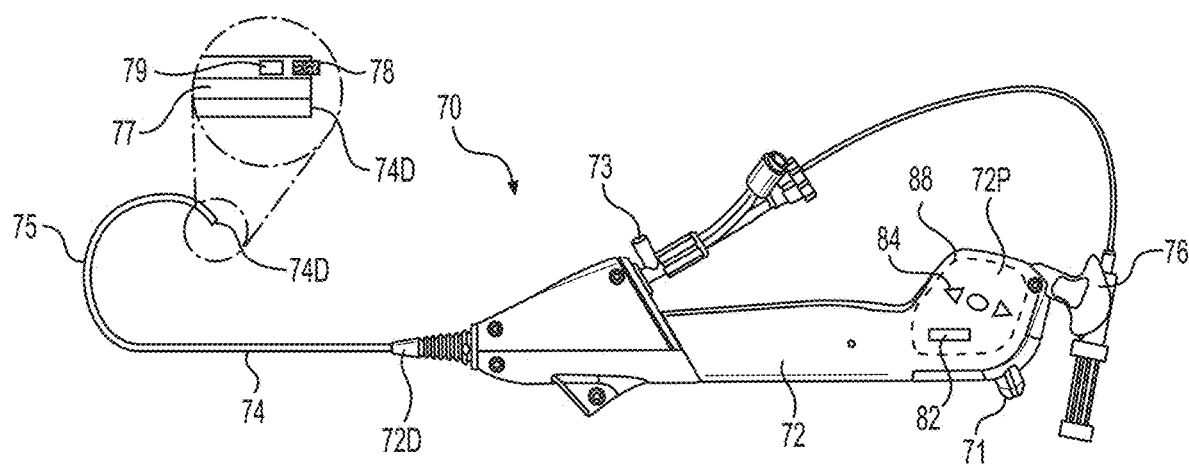
FIG. 6A depicts aspects of an exemplary treatment device.

The one or more treatment devices 62 may include (or be delivered with) a scope 70 configured for use in noninvasive procedures, such as any ureteroscope sold by Boston Scientific® under the brand name LithoVue®. As shown in FIG. 6A, for example, scope 70 may comprise a scope body 72 extending between a proximal end 72P and a distal end 72D, and a scope sheath 74 extending distally from end 72D. A working channel 77 may extend from a port 73 on scope body 72, through scope body 72 and scope sheath 74, and out of a distal end 74D of sheath 74, allowing for delivery of one or more treatment devices 62 to a treatment site 32 through working channel 77 (e.g., FIG. 3). Fluids from one or more source elements 68 also may be delivered to site 32 through working channel 77. As also shown in FIG. 6A, scope may 70 further comprise: one or more scope actuators 71 configured to manipulate portions of sheath 74, such as steerable portion 75; a delivery mechanism 76 configured to move another device (e.g., an elongated tool or laser fiber) relative to scope body 72 (e.g., inside or outside of channel 77). Any sensor 61, treatment device 62, and/or imaging device 69 may be located on distal end 74D of sheath 74. For example, distal end 74D of FIG. 6A includes an imaging element 78; and a locator beacon 79. Exemplary uses for scope 70 are described further below.

An exemplary input device 80 is depicted in FIG. 1 as being configured to operate display 10 via processing unit 50. As shown, input device 80 may comprise: a transceiver 82; and a display actuator 84. Transceiver 82, like transceiver 55, may be configured to establish and maintain a communication between input device 80 and processing unit 50 using any known technologies, wired or wireless. Display actuator 84 may be utilized to operate display 10 in response to a user-generated signal. As shown in FIG. 1, for example, display actuator 84 may comprise a plurality of buttons that are configured to operate display 10 in response to user-generated tactile signals, like a remote control or computer mouse. In this example, display actuator 84 is positioned adjacent to the one or more scope actuators 71, allowing for single-handed use of scope actuators 71 and display actuator 84.

Transceiver 82 and/or display actuator 84 may be mounted on scope body 72. In FIG. 1, for example, transceiver 82 and actuator 84 are attached to an input module 88 that is removably mounted to proximal end 72P of scope body 72. In this configuration, input module 88 may be swapped out and/or used interchangeably with a plurality of scopes 70, providing user 1 with the opportunity to replace, upgrade, and/or customize input device 80.

As described herein, base system 100 may be uniquely configured to realize operating room benefits by leveraging the capabilities of any device described herein, individually and/or in combination. For example, by utilizing processing unit 50 to obtain and/or access various computer applications for operating these devices (e.g., from data sources 67), system 100 may be further configured to utilize and/or enhance the capabilities of each device, and/or create new combinations of these capabilities. As a further example, by providing an application store (e.g., data sources 67), system 100 also promotes development and support of these computer applications by a greater development community, including doctors seeking medical advances, and software developers seeking technological advances. Different benefits of system 100 may be realized during the preoperative, intraoperative, and postoperative stages of a procedure, such as a urological procedure. Many exemplary benefits are now described with reference to methods 200, 300, and 400.

Exemplary uses for base system 100 are now described with reference to method 200, which may be a preoperative method. As shown in FIG. 2A, method 200 may comprise: (210) receiving, at processing unit 50, data associated with a patient; (220) determining, with processing unit 50, a treatment for the patient; (230) identifying, with processing unit 50, control settings associated with one or more treatment devices 62 that are (i) in communication with processing unit 50, and (ii) operable to perform the treatment; and (240) generating, with processing unit 50, display 10 to include the control settings and at least one view of the data.

Method 200 may comprise intermediate steps for receiving data from one or more data sources. As noted above, display 10 may be based on any data associated with a patient, including one or more of the following data types: (i) image data; (ii) sensor data; and (iii) geometric data; and processing unit 50 may be configured to receive the data in real-time or in advance, from any data source, local or remote. Accordingly, receiving step 210 may comprise receiving the data from any data source, including any intermediate steps required to establish a communication between processing unit 50 and the data source. For example, step 210 may comprise: establishing a communication with data sources 67, and obtaining the data therefrom.

Receiving step 210 may include data gathering steps. For example, receiving step 210 may comprise: generating image data (e.g., X-ray images) with one more imaging sources 69 in advance of a procedure, storing the image data on imaging sources 69 and/or data sources 67, and/or obtaining the image data from sources 69 and/or 67. If the image data is to be received in real-time, then receiving step 210 may comprise: establishing a communication with the imaging devices 69 (e.g., imaging element 78 of scope 70), and receiving the image data therefrom (e.g., as a real-time video feed). The sensor data may be similarly obtained from one or more sensors 61, such that receiving step 210 comprises: establishing a communication with and receiving sensor data from one or more sensors 61. For example, sensors 61 may include one or more of an ultrasound transducer, a pressure sensor, a light sensor, an irradiation sensor, or like sensor, each sensor 61 being configured to output sensor data, wherein receiving step 210 comprises receiving the data.

Geometric data may be received or generated in receiving step 210. For example, geometric data including a three-dimensional model of the patient, or a portion of the patient, may be generated in advance of a procedure and stored on a data source 67, such that receiving step 210 comprises: receiving the three-dimensional model from the data source 67; and selecting the at least one view from the three-dimensional model. Processing unit 50 may comprise a graphics module 57 (e.g., FIG. 5) configured to generate the three-dimensional model from data associated with the patient, such as the image or sensor data described above. Accordingly, receiving step 210 also may comprise: receiving image or sensor data associated with the patient, and generating the three-dimensional model with graphics module 57 based on said data. For example, the image data may include a plurality of X-ray images of patient, each taken at different positions and/or angles, and receiving step 210 may comprise generating the three-dimensional model by stitching the plurality of X-ray images together relative to one or more reference points of the patient, such as the location of a kidney (e.g., FIG. 3). As a further example, the sensor data may include an output from an ultrasound transducer configured to output localized representations of a path extending through the patient (e.g., path 22 of FIG. 3), and step 210 may comprise generating the three-dimensional model by combining the localized representations.

Step 210 may comprise generating the three-dimensional model using one or more computer applications. For example, receiving step 210 may comprise: analyzing the image and/or sensor data to identify a computer application configured to generate a three-dimensional model of the patient with said data; obtaining the identified application from data sources 67; and generating the three-dimensional model from said data with the application. Graphics module 57, for example, may be configured to execute the computer application using image and/or sensor data stored local or remote to memory 52.

Method 200 may be utilized to enrich the three-dimensional model. For example, receiving step 210 may comprise: identifying capabilities of one or more sensors 61 and/or imaging sources 69 in communication with processing unit 50; identifying one or more computer applications configured to generate layers for the three-dimensional model with the identified capabilities; and incorporating these layers into the model. For a urology procedure, for example, step 210 may comprise: identifying capabilities of sensors 61 and devices 69; identifying a stone identification application configured to map locations and characteristics of each stone at a treatment site 32 using the identified capabilities; utilizing the stone identification application to generate a layer including the mapped locations and characteristics; and incorporating the layer into map view 30. Additional examples are described below.

Figure 3:
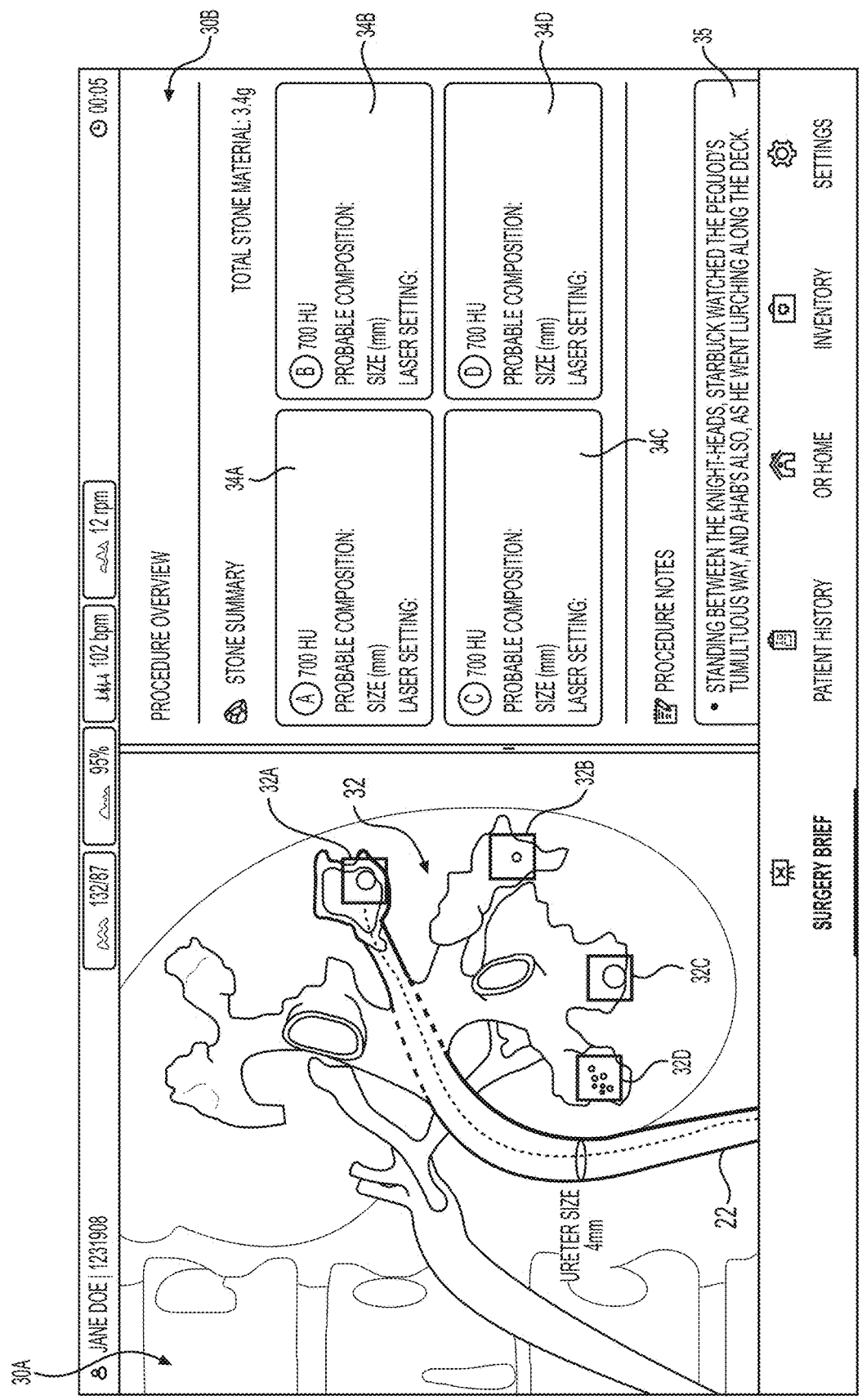
FIG. 3 depicts aspects of an exemplary display.

Determining step 220 may include intermediate planning steps. As shown in FIG. 3, for example, step 220 may comprise expanding map view 30 to include a selection portion 30A and a planning portion 30B. Selection portion 30A may be based on a three-dimensional model of the patient, and operable to identify a treatment site 32; and planning portion 30B may be based on planning portion 30A, and operable to identify characteristics of, and potential treatments for, the treatment site 32. In FIG. 3, for example, four exemplary treatment sites 32A, 34B, 34C, and 34D are identified in selection portion 30A; and planning portion 30B includes a listing 34A, 34B, 34C, or 34D of potential laser energy treatments for each treatment site 32A-D. Accordingly, step 220 may further comprise: identifying a treatment site 32; locating one or more objects (e.g., a kidney stone) at site 32; determining a composition of each located object; and generating a list of potential treatments based on the composition.

Aspects of determining step 220 may be responsive to user-generated signals, such as a first tactile signal for operating portion 30A with display device 60, and/or a second tactile signal for operating portion 30B with input device 80. A computer application may be used to perform any portion of determining step 220. For example, the stone identification program described above may be used in step 220 to automatically identify and locate stones at each treatment site 32A-D based on image and/or sensor data. At any point in step 220, additional information 35 (e.g., procedure notes) also may be automatically and/or manually associated with each treatment site 32A-D and/or listing of potential treatments 34A-D.

Step 220 may include intermediate configuration steps. For example, as with other method steps described herein, determining step 220 may comprise: identifying capabilities of one or more sensors 61 in communication with processing unit 50; identifying one or more computer applications configured to leverage the identified capabilities; and/or obtaining the one or more computer applications. For a urology procedure, for example, step 220 may comprise: identifying the capabilities of any sensors 61 configured to detect heat and radiation at a treatment site 32; identifying a laser treatment application configured to control the discharge of laser energy in response to the detected heat and radiation; and obtaining the laser treatment application from data sources 67. Similar configured steps may be performed for any device described herein. Additional configuration steps also may comprise: updating planning views 34A-D; obtaining additional inputs for the aforementioned computer applications; and/or selecting or enabling selection of potential treatments using display device(s) 60 and/or input device 80.

Identifying step 230 may include intermediate steps for receiving control settings for the one or more treatment devices 62. The control settings may be received directly from each device 62. For example, step 230 may comprise receiving the control settings directly from each treatment device 62 during a handshaking process performed to establish communication with processing unit 50. In some aspects, the control settings may be obtained from one or more data sources 67. For example, step 230 also may comprise obtaining a device identifier from each treatment device 62 (e.g., during the handshaking process); delivering the device identifier to data sources 67; and receiving the control settings therefrom. The device identifier also may be used to promote the development of additional settings. For example, the identifier may be associated with a device specification that can be utilized by third-party developers to develop new control settings, and processing unit 50 may be configured to make those developments available for immediate use via sources 67.

A computer application may be used to determine the control settings. For example, identifying step 230 may comprise: identifying capabilities of one or more treatment devices 62 in communication with processing unit 50; identifying one or more computer applications configured to generate a procedure-specific set of control settings based on identified capabilities; and/or obtaining the one or more computer applications. For a urology procedure, for example, identifying step 230 may comprise: identifying the capabilities of a fluid source configured to deliver fluid to a treatment site 32; identifying a urology-specific fluid management application configured to generate control settings for controlling the fluid source; and/or obtaining the fluid management application from data sources 67. New and/or combined capabilities may be realized in this manner. For example, step 230 may comprise utilizing said computer applications to generate control settings for operating a first treatment device 62 together with a second treatment device 62 to perform a particular treatment. In keeping with the previous urology example, step 230 may further comprise: identifying the capabilities of a laser source configured to discharge laser energy to the treatment site 32; identifying a treatment application configured to generate control settings for controlling the laser source together with the fluid source to perform a treatment; and obtaining the treatment application from data sources 67.

Generating step 240 may include intermediate steps for generating display 10. In some aspects, step 240 may comprise: identifying a location 24 (e.g., FIG. 4A) of treatment device 62 in the at least one view of display 10; and tracking movements of the identified location 24 in said at least one view. Locator beacon 79 of scope 70 may be used to identify location 24. For example, as shown in FIG. 5, processing unit 50 may comprise a tracking module 58 configured to identify and track locator beacon 79, such that step 240 comprises establishing a communication between module 58 and beacon 79, and identifying location 24 therewith. One or more sensor 61 and/or one or more imaging devices 69 also may be utilized to establish location 24 in step 240, with or without locator beacon 79. For example, portions of sheath 74 of scope 70 may include a radiopaque material that can be tracked using a fluoroscope. Additional steps for configuring display 10 for use with display devices 60 also may be performed.

Other uses for system 100 are now described with reference to method 300 of FIG. 2B, which may be an intraoperative method. As shown, method 300 may comprise: (310) generating, with processing unit 50, a display 10 including control settings for a treatment device 62 (e.g., control view 40) and at least one view of data associated with a patient (e.g., navigation view 20 or map view 30); (320) overlaying onto the least one view, with processing unit 50, depictions of (i) a treatment site 32, (ii) a path 22 to the treatment site 32, and (iii) a location 24 of the treatment device 62 on the path 22; (330) moving the treatment device 62 along path 22 responsive to display 10, and continuously updating display 10 with processing unit 50 responsive to the movements, until location 24 arrives at treatment site 32; (340) obtaining, with processing unit 50, an input responsive to the control settings; and (350) operating, with processing unit 50, device 62 according to the input and the control settings.

Generating step 310 may include intermediate steps for configuring display 10, including any steps described above with respect to generating step 240 of method 200. For example, generating step 310 may comprise identifying location 24, establishing communications between tracking module 58 and locator beacon 79, and/or configuring display 10 for use with one or more display devices 60.

Overlaying step 320 may be utilized to augment display 10. Navigation view 20 of FIG. 4A, for example, may comprise a background layer generated from fluoroscopic images of the patient. In this example, overlying step 320 may comprise: generating a foreground layer including graphical depictions of treatment site 32, path 22 and location 24; and overlying the foreground layer onto the background layer. Another example is provided by map view 30 of FIG. 4B, which includes a background layer generated from a view of the three-dimensional model, and a foreground layer including a graphical depiction of path 22 and treatment sites 32A-D. The locations of path 22 and treatment sites 32A-D may be determined in step 320. For example, the location of path 22 and treatment area 32 may be determined using step 220 of method 200 described above; and/or a computer application may be obtained by processing unit 50 for that purpose. As noted above, locator beacon 79, sensors 61, and/or imaging devices 69 may be used to establish and track location 24.

Overlaying step 320 also may include intermediate steps for selecting or "tagging" portions of display 10. One example is provided in FIG. 4B, wherein the background layer is generated from a video feed output by imaging element 78 of scope 70, and the foreground layer includes wire-frame depictions of interior surfaces of path 22. In this example, overlying step 320 may comprise: overlaying a wire-frame grid 25 onto the interior surfaces of path 22 so as to define a plurality of surface areas 26; selecting one or more of the surface areas 26; and identifying the selected areas in navigation view 20 and/or map view 30. One or more sensors 61 may be used in step 320 to automatically tag one or more surface areas 26. For example, step 320 may further comprise: scanning each surface area 26; and tagging each surface area 26 that meets a predetermined scan criteria. For a urology procedure, for example, overlaying step 230 may comprise: scanning each surface 26 with a sensor 61 to distinguish between a stone and tissue surrounding the stone; and tagging each area 26 having a stone density greater than a predetermined maximum. Similar to above, processing unit 50 may be further configured to obtain one or more computer applications that are operable to perform aspects of step 320, such as scanning each surface area 26 with sensors 61, imaging devices 69, or like devices.

Moving step 330 may include intermediate steps for using display 10 to guide movements of treatment device 62. As shown in FIG. 4B, for example, step 330 may comprise defining a path 22 towards one of treatment sites 32A-D; and moving treatment device 62 along the path 22 by tracking movements of location 24. Continuous communication between processing unit 50 and beacon 79, one or more sensors 61, or other tracking means may be required to simultaneously move treatment device 62, and update display 10 responsive to the movements. Accordingly, step 330 may further comprise intermediate steps for establishing such communications.

Moving step 330 also may include intermediate steps for operating scope 70 and/or delivery mechanism 76. As shown in FIG. 6A, for example, scope 70 includes scope actuator 71, which is configured to manipulate steering portion 75 of sheath 74; and delivery mechanism 76, which is configured to move a treatment device relative to scope 70, such as a laser fiber. Actuator 71 and/or delivery mechanism 76 may include electric actuators, such that method step 330 comprises: receiving a movement signal from display 10 and/or input device 80; and moving device 62 towards the area 32 along path 22 by operating said electric actuators according to the movement signal. Similar to above, one or more computer applications may be used to generate the motion signal, such that step 330 further comprises any intermediate steps for identifying movement capabilities for actuator 71 and/or delivery mechanism 76; and identifying one or more computer applications configured to move treatment device 62 using said capabilities. For a urological procedure, for example, one computer application may be configured to: translate geometric data associated with path 22 into a motion signal; and automatically move device 62 through path 22 by operating actuator 71 and/or mechanism 76 based on the motion signal.

Obtaining step 340 may be utilized to obtain whatever inputs are necessary for operating treatment device 62 (or other device described herein). For example, obtaining step 340 may comprise receiving an input from user 1 including at least one of an audio signal, a tactile signal, and a visual signal; converting the input into a control signal; and outputting the control signal. Each signal may be user-generated and/or specific to treatment types, power levels, times, or like quantity. In some aspects, display 10 and/or input device 80 may be configured to receive the input. For example, control view 40 may be output to a display device 60, and the configuration of display actuator 84 may correspond with the configuration of control view 40, such that either display 10 or input device 80 may be utilized to receive a similar tactile signal. One or more sensors 61 also may be configured to receive the input. For example, sensors 61 may include a movement sensor configured to receive a visual signal by tracking movements of display actuator 84 and/or a portion of user 1.

Obtaining step 340 may comprise intermediate steps for modifying the control signal. For example, obtaining step 340 may comprise: identifying an object at a treatment area 32; determining a characteristic of the identified object with one or more sensors 61; and modifying the control signal based on the determined characteristic. Any characteristic may be determined and utilized within step 340, and any number of computer applications may be used to make these determinations. One example is depicted in FIG. 4C, which includes a background layer is generated by imaging element 78 to include a close-up view of stones at site 32A, and a foreground layer generated by sensors 61 to include a measure of stone burden 35 (e.g., shown as an outline of each stone at site 32A); a measurement of stone size 36 (e.g., shown as a measurement relative to a center of each stone); and/or an indication of stone type (e.g., shown as an indicator at or adjacent each stone). In this example, sensors 61 may include an ultrasound transducer located inside or outside of the body, and the measure of stone burden 35, stone size 36, and/or stone type may be generated by processing unit 50 with a stone identification application configured for use with the transducer. Accordingly, step 340 may comprise modifying the control signal based on measure of stone burden 35, size 36, and/or type. Other applications may be used to modify the signal based on other characteristics.

Operating step 350 may be utilized to apply the treatment energy. At this point in method 300, all of the control settings may have been determined, such that step 350 comprises: activating treatment device 62 with activation switch 42 of control view 40 and/or display actuator 84 of input device 80; and discharging the treatment energy towards a targeted object at the treatment site 32. Similar to above, operating step 350 may comprise intermediate modification steps. For example, control view 40 of FIG. 4B may be used to manually adjust the treatment energy in step 350 by operation of adjustment buttons 45A and 45B, both of which are configured to tune specific aspects of the treatment energy. For a urology procedure, for example, treatment device 62 may be configured to deliver laser energy, adjustment button 45A may be used to control a power level for the laser energy and adjustment button 46A may be used to control a frequency, pulse rate, or other characteristic of the laser energy.

Method 300 may be utilized to establish a control loop for one or more treatment devices 62, such as a feedback control loop that modifies an output of a treatment device 62 responsive to a feedback signal generated by a sensor 61. For example, operating step 350 may comprise: determining a characteristic of the targeted object with one or more sensors 61; and modifying a treatment energy based on the determined characteristic. For a urology procedure, for example, treatment device 62 may be configured to discharge laser energy toward a stone located at a treatment site 32, and operating step 350 may comprise: receiving a reflected portion of the laser energy from the stone and/or site 32; analyzing the reflected portion with one or more sensor 61; and modifying the laser energy responsive to an output from sensors 61. In this example, the feedback control loop may prevent unwanted tissue damage by stopping or tapering the discharge of the laser energy if/when the output from sensors 61 indicates that the stone has been destroyed. Similar control loops may be established for any device described herein. Continuing the previous urology example, source elements 68 may include a fluid or medicine source, and step 350 may comprise: analyzing a characteristic of site 32 with one of sensors 61, such as internal pressure or irradiation levels; and modifying an amount of fluid or medicine flow responsive to the output from the sensor 61. One or more computer applications may be used to establish the feedback control loops, such that operating step 350 may include any intermediate steps for identifying, obtaining, and utilizing the applications.

Still other exemplary uses for system 100 are now described with reference to method 400, which may be a postoperative method. As shown in FIG. 2C, for example, method 400 may comprise: (410) recording data associated with a performed treatment; (420) generating one or more reports based on recorded data; (430) outputting the one or more reports to data source 67.

Recording step 410 may include, for example, intermediate steps for recording any data generated during the performance of methods 200 and 300. The recorded data may assume any form. For example, recording step 410 may comprise generating a video stream of display 10 during a procedure, thereby recording each selection, input, or output relative thereto. Because display 10 includes at least one view of data associated with the patient (e.g., navigation view 20 and/or map view 30), and a view of the associated control settings (e.g., control view 40), said video stream may be used to archive any number of decisions by user 1 and/or system 100. The recorded data also may include any data generated by one or more patient monitors 63 (e.g., a vital signs monitor), and/or one or more operating room monitors 64 (e.g., an observation camera). For example, in step 410, one operating room monitor 64 may be configured to record a quantum of materials used during a procedure by tracking the usage and/or weight of each device in the operating room.

Reporting step 420 may be utilized to perform various archival functions with the recorded data. For example, reporting step 420 may comprise: analyzing the recorded data; and generating one or more reports therefrom. In one aspect, the one or more reports may be utilized to improve operating room efficiency by, for example, automatically summarizing treatments, treatment times, results, and like performance measures, any of which may be utilized to realize operating room benefits. These reports also may be used for inventory management purposes. For example, reporting step 420 may comprise: generating a report based on the quantum of materials used during the procedure; and delivering the report to a third party for automatic restocking of said materials. The quantum of materials may be determined from a user input, or with one or more operating room monitors 64, as noted above.

Sending step 430 may be utilized to archive the recorded data and/or one or more reports for future use. For example, step 430 may comprise: sending the recorded data and/or one or more reports to memory 52 and/or data sources 67 together with a patient identifier, such as a reference number associated with the patient's electronic medical records, like a social security number. Some portion of the recorded data and/or one or more reports also may be output to data source 67 without the patient identifier for use in various statistical reports.

Figure 6B:
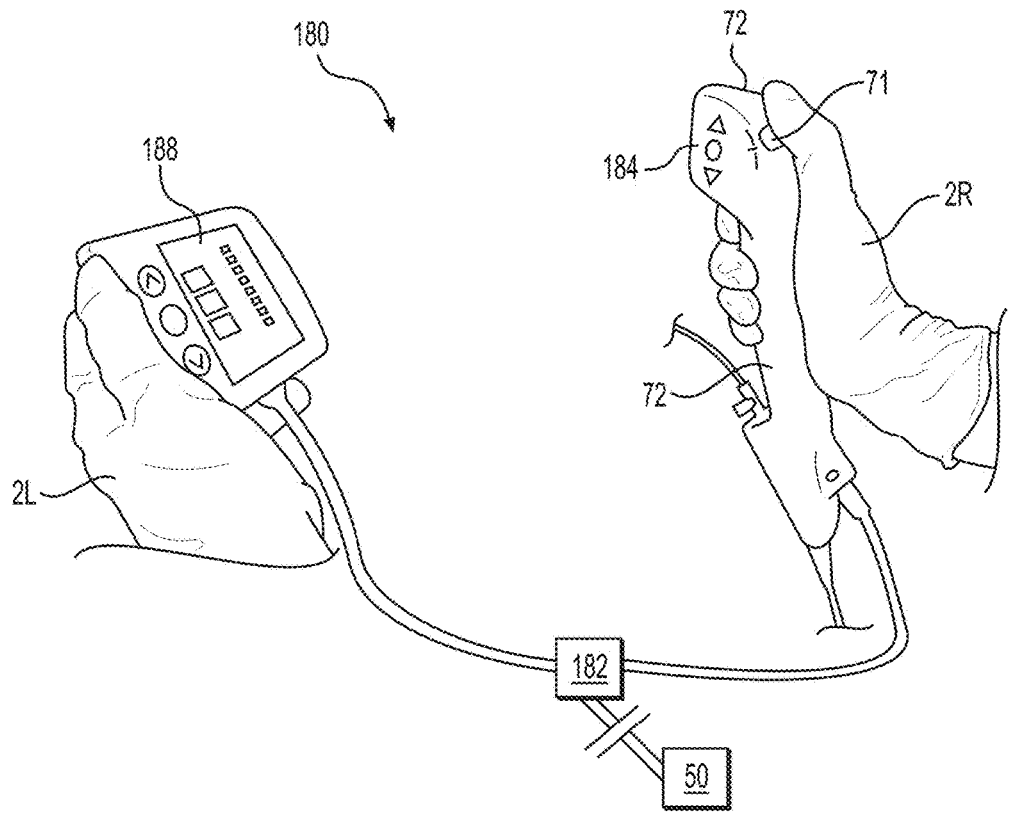
FIG. 6B depicts aspects of an exemplary input device.
Figure 7:
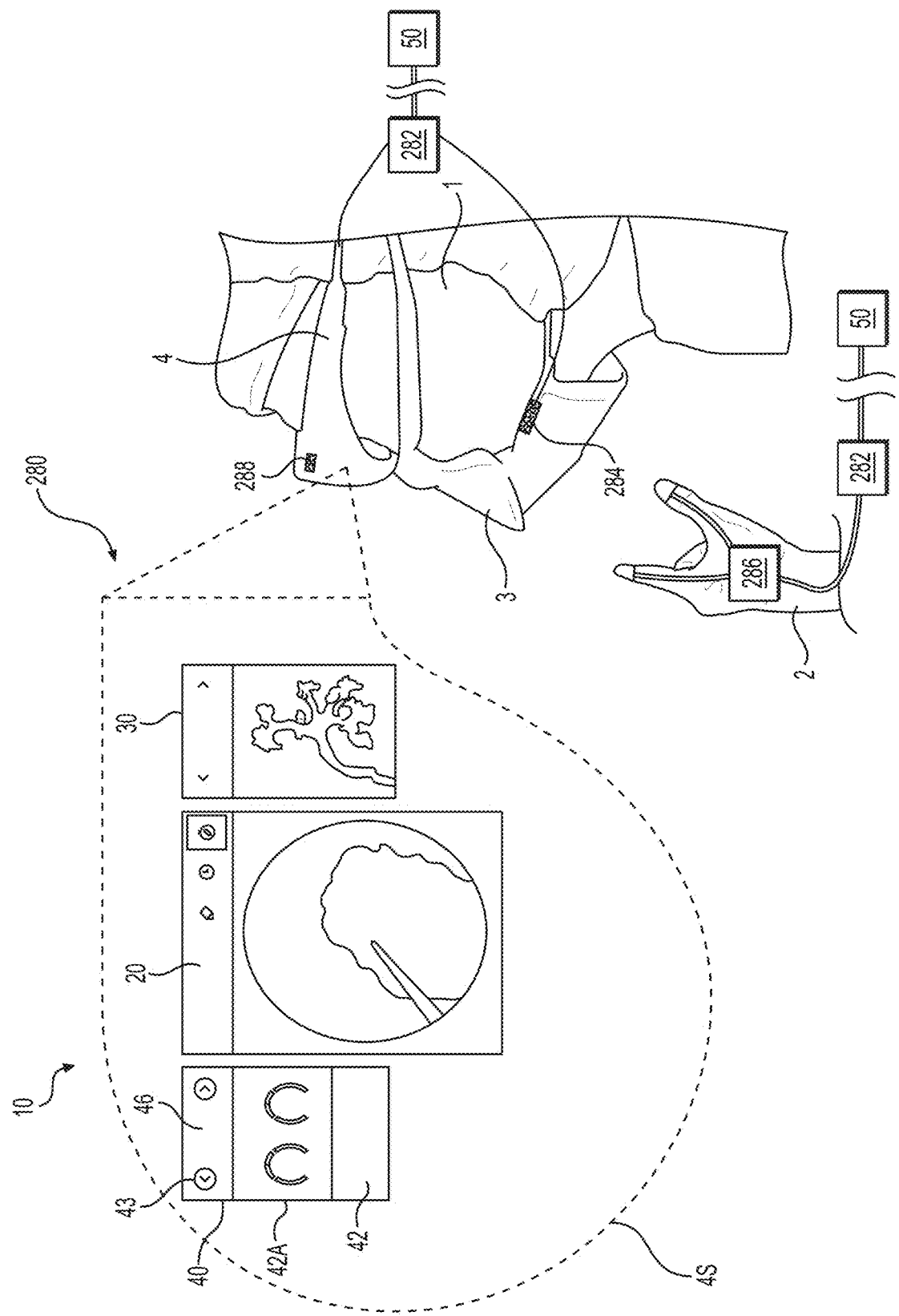
FIG. 7 depicts aspects of another exemplary control device.

Additional aspects of system 100 are now described with reference to input device 180 of FIG. 6B, and input device 280 of FIG. 7, both of which are configured to operate display 10 via processing unit 50. As shown in FIG. 6B, input device 180 may comprise a transceiver 182; a first display actuator 184; and a second display actuator 188. Transceiver 182 may be configured to establish and maintain a communication between input device 180 and processing unit 50 using any known technologies, wired or wireless. First and second display actuators 184 and 188 are configured to operate display 10 in response to an input from user 1. As shown FIG. 6B, first actuator 184, like display actuator 84, may comprise a plurality of buttons mounted on scope body 72, allowing for generalized control of display 10; whereas second display actuator 188 may comprise a touch-sensitive screen, allowing for specialized control of display 10. In FIG. 6B, for example, various means for activating a treatment energy (e.g., laser energy) may be depicted with control view 40, while various for modifying the treatment energy may be depicted with second actuator 188. In another example, control view 40 may be switchable between control settings for various treatment devices 62, while second actuator 188 remains dedicated to the control settings for one device.

Aspects of input device 280 may be configured for hands-free operation of display 10 within the sterile field. As shown in FIG. 7, for example, input device 280 may include a portion of sensors 61, such as one or more of an audio sensor 284, a gesture sensor 286, and/or a visual sensor 288. In FIG. 7, one audio sensor 284 is a microphone that is mounted on mask 3 and configured to receive voice commands, such as an activation command corresponding with switch 42. As shown, gesture sensor 286 includes motion sensors that are associated with digits of hand 2, configured to receive visual signals by tracking movements of the digits, such as pinching motion utilized for zooming into navigation view 20. Gesture sensor 286 also may include any type of camera or motion sensor configured to receive the hand signals by visually observing hand 2. In one aspects, sensor 286 includes a camera that is mounted on mask 3, glasses 4, or another portion of user 1 and aimed at hand 2. For example, hand 2 may include a glove with motion tracking pattern, and sensor 286 may be configured to output a motion signal by recognizing the pattern and tracking relative movements of hand 2 therewith.

Visual sensor 288 may include any type of camera or motion sensor, any of which may be operable with any type of display device 60. As shown in FIG. 7, for example, display device 60 may comprise a projector that is mounted on glasses 4 and configured to output display 10 into the field of view of at least one eye of user 1. The projector may output display 10 onto an interior surface 4S of glasses 4, as in FIG. 7; or output display 10 directly into the at least one eye, such as directly into the retina. Visual sensor 288 may comprise an eye movement sensor configured to generate visual signals by tracking movements of eye. For example, a visual selection signal may be determined by focusing the eye on a portion of display 10 for a predetermined period of time. The depiction of glasses 4 in FIG. 7 is exemplary, and any type of head mount may be used to ensure that display 10 remains in view. Ceiling or wall mounts also may be used, as may any mounting structure engageable with scope 70.

Numerous benefits may be realized with aspects of the operating room devices, methods, and systems described herein. For example, aspects of system 100 may be configured to increase operating room efficiency, reduce burdens placed on operating room assistants and administrative staff, and improve patient safety, all without sacrificing desirable outcomes. According to this disclosure, some benefits may be realized by utilizing system 100 as a hub configured to communicate with a plurality of devices local to or remote from the operating room, and generate display 10 as one means for controlling at least some of those devices from a position inside the operating room, such as behind a sterile field. Other benefits may be realized by expanding the capabilities of system 100 to account for the unique capabilities of each device in communication therewith, such as sensors 61, treatment devices 62, and/or imaging devices 69, any of which may be used to generate data associated with the patient, generate or modify a three-dimensional model of the patient with said data, analyze portions of the data, and/or perform like functions, any of which may be further expanded by use of one or more computer applications.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A method comprising:
   receiving, at a processing unit, data associated with a patient;
   determining, with the processing unit, a treatment for the patient;
   identifying, with the processing unit, control settings associated with one or more treatment devices that are (i) in communication with the processing unit, and (ii) operable to perform the treatment; and
   generating, with the processing unit, a display including the control settings and at least one view of the data,
   wherein the identifying step further comprises:
      receiving, at the processing unit, an identifier from the one or more treatment devices;
      delivering, with the processing unit, the identifier to a data source; and
      receiving, at the processing unit, the control settings from the data source.

2. The method of claim 1, wherein the data includes a three-dimensional model of a portion the patient, and the receiving step comprises:
   receiving, at the processing unit, the three-dimensional model from a data source; and
   generating, with the processing unit, the at least one view from the three-dimensional model.

3. The method of claim 1, wherein the data includes images of the patient, and the receiving step comprises:
   receiving, at the processing unit, the images from a data source; and
   generating, with the processing unit, a three-dimensional model of the patient from the images.

4. The method of claim 1, wherein the determining step further comprises:
   identifying, with the processing unit, potential treatments for the patient;
   determining, with the processing unit, whether the one or more treatment devices are operable to perform any of the potential treatments; and generating, with the processing unit, the display to include a listing of the potential treatments performable by the one or more treatment devices.

5. The method of claim 1, wherein the identifying step further comprises obtaining, with the processing unit, the control settings from the one or more treatment devices.

6. The method of claim 1, wherein the one or more treatment devices include a first treatment device in communication with the processing unit and a second treatment device in communication with the processing unit, and the identifying step further comprises:
receiving, at the processing unit, a first control setting for the first treatment device and a second control setting for the second treatment device; and
identifying, with the processing unit, one or more computer applications for operating the first and second treatment devices in a coordinated manner to perform a treatment such that the identifying step includes:
delivering, with the processing unit, the first and second control settings to a data source; and
receiving, from the data source, the one or more applications.

7. The method of claim 1, wherein the at least one view of the display includes a first view different from a second view, and the generating step comprises:
positioning a distal end of the one or more treatment devices in the patient; and
locating, with the processing unit, said distal end in the first and second views; and
wherein the data includes images of interior surfaces of the patient, the first view includes the interior surfaces, and the method comprises:
overlaying, with the processing unit, a grid onto the interior surfaces depicted in the first view;
tagging, with the processing unit, one or more areas defined by the grid; and
locating, with the processing unit, the tagged area in the second view.

8. The method of claim 1, further comprising:
receiving, with the processing unit, an input from an input device in communication with processing unit;
operating, with the processing unit, the one or more treatment devices according to the input and the control setting;
identifying, with the processing unit, an object in the patient;
determining, with the processing unit, a characteristic of the object using at least one sensor;
modifying, with the processing unit, the input or the control settings based on the characteristic;
generating, with the processing unit, one or more reports including the control settings and the input; and
outputting, with the processing unit, the one or more reports,
wherein the input is a user-generated signal including at least one of an audio signal, a tactile signal, and a visual signal.

9. A method comprising:
generating, with a processing unit, a display including control settings for a treatment device and at least one view of data associated with a patient;
overlaying onto the at least one view, with the processing unit, depictions of (i) a treatment site, (ii) a path to the treatment site, and (iii) a location of the treatment device on the path;
moving the treatment device along the path responsive to the at least one view, and continuously updating the display with the processing unit responsive to the movements, until the location of treatment device arrives at the treatment site;
obtaining from an input device, with the processing unit, an input responsive to the control settings; and
operating, with the processing unit, the treatment device to apply a treatment energy at the treatment site according to the input and the control settings.

10. The method of claim 9, wherein the input comprises a user-generated signal including at least one of an audio signal, a tactile signal, and a visual signal, and the method further comprises:
converting, with the processing unit, the user-generated signal into a control signal;
outputting, with the processing unit, the control unit to the treatment device;
determining, with the processing unit, a characteristic of the object or the treatment energy using at least one sensor;
modifying, with the processing unit, the control signal based on the determined characteristic;
obtaining, with the processing unit, a computer application configured for use with the at least one sensor; and
determining, with the processing unit, the characteristic with the computer application and the at least one sensor.

11. The method of claim 10, wherein the object includes one or more stones, the characteristic includes a measure of stone burden, stone size, or stone burden associated with the one or more stones, and the computer application is configured to modify the control signal based on the measure; and
wherein the characteristic includes a composition of the one or more stones, and the computer application is configured to further modify the control signal based on the composition.

12. The method of claim 11, wherein the treatment energy is a laser energy, the characteristic includes a measure of the laser energy, and the computer application is configured to modify the control signal based on the measure of laser energy.

13. A system comprising:
a processing unit in communication with one or more treatment devices;
a display generated by the processing unit to comprise:
at least one view of data associated with a patient; and
a control setting for the one or more treatment devices; and
an input device operable with the display to activate the one or more treatment devices.

14. The system of claim 13, wherein the processing unit is configured to:
obtain the data from a data source; and
obtain the control setting from the one or more treatment devices or the data source.

15. The system of claim 14, wherein the data includes a three-dimensional model of a portion of the patient, and the processing unit is configured to generate the at least one view based on three-dimensional model; and
wherein the processing unit is configured to:
obtain, from the data source, a computer application configured to generate the three-dimensional model; and
generate the three-dimensional model using the computer application.

16. The system of claim 13, wherein the processing unit is configured to:

identify capabilities associated with the one or more treatment devices;

obtain, from a data source, a computer application based on the identified capabilities; and generate the control settings with the computer application; and wherein one or more treatment devices include a first treatment device and a second treatment device, and the control settings include at least one option for operating the first and second treatment devices in a coordinated manner to perform a treatment; and wherein the first treatment device is a laser source and the second treatment device is a fluid source.

17. The system of claim 16, wherein the treatment device includes a handle, and the input device includes a display actuator mounted on the handle and configured to receive a user-generated signal including at least one of audio signal, a tactile signal, and a visual signal;

wherein the treatment device is a scope, and the handle includes one or more actuators configured to operate a steerable portion of the scope; and wherein the system further comprises a display device configured to receive at least a portion of the display, wherein the display device is wearable on a hand of a user to permit operation of the one or more actuators with the same hand.

18. The system of claim 13, wherein the input device includes at least one sensor configured to receive the user-generated signal, and wherein the at least one sensor includes a movement sensor configured to receive the visual signal by tracking movements of a user.

19. The system of claim 18, further comprising a projector configured to output the display onto a surface, wherein the movement sensor includes an eye movement sensor configured to receive the visual by tracking movements of at least one eye of a user, and wherein the surface is head-mounted so as to position the display within a field of view of the least one eye.

* * * * *